US009857312B2

(12) United States Patent
Lev et al.

(10) Patent No.: US 9,857,312 B2
(45) Date of Patent: Jan. 2, 2018

(54) OPTICAL INSPECTION SYSTEM USING MULTI-FACET IMAGING

(75) Inventors: Michael Lev, Yokneam (IL); Ehud Efrat, Zichron Yaakov (IL); Roni Flieswasser, grimbergen (BE)

(73) Assignee: CAMTEK LTD., Migdal Haemeq (IL)

( * ) Notice: Subject to any disclaimer, the term of this patent is extended or adjusted under 35 U.S.C. 154(b) by 2290 days.

(21) Appl. No.: 12/664,671

(22) PCT Filed: Jun. 15, 2008

(86) PCT No.: PCT/IL2008/000815
§ 371 (c)(1),
(2), (4) Date: Dec. 28, 2010

(87) PCT Pub. No.: WO2008/152648
PCT Pub. Date: Dec. 18, 2008

(65) Prior Publication Data
US 2011/0141267 A1    Jun. 16, 2011

Related U.S. Application Data

(60) Provisional application No. 60/944,106, filed on Jun. 15, 2007, provisional application No. 60/955,371, filed on Aug. 12, 2007.

(51) Int. Cl.
*G01N 21/95* (2006.01)
*G01N 21/88* (2006.01)

(52) U.S. Cl.
CPC ..... *G01N 21/9503* (2013.01); *G01N 21/8806* (2013.01)

(58) Field of Classification Search
None
See application file for complete search history.

(56) References Cited

U.S. PATENT DOCUMENTS

| 2007/0057164 A1* | 3/2007 | Vaughnn | H04N 5/2254 250/216 |
| 2009/0046298 A1* | 2/2009 | Betzig | G01N 21/6445 356/521 |
| 2010/0012818 A1* | 1/2010 | Baker | G01J 9/00 250/201.9 |

FOREIGN PATENT DOCUMENTS

TW        572295 U    6/2003

* cited by examiner

*Primary Examiner* — Eileen Adams
(74) *Attorney, Agent, or Firm* — Reches Patents

(57) ABSTRACT

An optical inspection system, the system includes: (i) an image sensor; and (ii) a single optical element, that at least partially surrounds an edge of an inspected object; wherein the optical element is adapted to direct light from different areas of the edge of the inspected object towards the image sensor so that the image sensor concurrently obtains images of the different areas.

24 Claims, 16 Drawing Sheets

Illuminating the edge of the inspected object. 610

Directing light, by optics positioned between the edge of the inspected object and an image sensor, towards an image sensor and reducing a length difference between different optical paths defined between different imaged areas of the edge of the inspected object and the image sensor. The optics include: a top optical element that directs light from at least one area out of a top area, a top bevel area and an apex of the edge of the inspected object towards the image sensor; and a bottom optical element that directs light from at least one area out of a bottom area, a bottom bevel area and an apex of the edge of the inspected object towards the image sensor. 920

Concurrently acquiring images, by the image sensor, of the different imaged areas. 930

Storing and additionally or alternatively processing the acquired images. The processing can be executed as part of a defect detection process during which defects of the edge of the inspected object are detected. 666

900    FIG. 16

OPTICAL INSPECTION SYSTEM USING MULTI-FACET IMAGING

RELATED APPLICATIONS

This application is a National Phase Application of PCT International Application Publication Number WO 2008/152648, International Filing Date Jun. 15, 2008, claiming priority of Unites States Provisional Patent Application Ser. No. 60/944106, filed Jun. 15, 2007, and claiming priority of Unites States Provisional Patent Application Ser. No. 60/955371, filed Aug. 12, 2007.

FIELD OF THE INVENTION

The invention relates to optical inspections of objects such as but not limited to wafers.

BACKGROUND OF THE INVENTION

Backside and edge/bevel defects are among those that have silently crept up to the surface of the world of yield-limiting defects. The presence of contamination at the backside of a wafer can compromise up to 10% yield of today's advanced semiconductor devices at multiple process steps such as lithography, diffusion, cleans, CMP, and CVD film deposition. Backside defects are not limited to contamination and damage and they also include mechanical scratches that can lead to wafer breakages in the subsequent high-temperature processes. With 300 mm wafers, significantly more real estate is located at the wafer edge. Edge-yield losses, typically 10 to 40% when normalized and compared to center die yield, has therefore become a major concern.

The increased automation (less manual handling) and the advanced topography requirement of solely using DSP (double side polished) wafers for 300 mm manufacturing also have driven more significant challenges to recognize systematic issues early in the production line.

SUMMARY

An optical inspection system that includes: an image sensor; and a single optical element, that at least partially surrounds an edge of an inspected object; wherein the optical element is adapted to direct light from different areas of the edge of the inspected object towards the image sensor so that the image sensor concurrently obtains images of the different areas.

An optical inspection system, the includes: an image sensor; and multiple optic fibers that are arranged such as to at least partially surround an edge of an inspected object; wherein the optic fibers are adapted to direct light from the different areas of the edge of the inspected object towards the image sensor so that the image sensor concurrently obtains images of the different areas.

An optical inspection system that includes: an image sensor adapted to concurrently acquire images of an apex of the edge of the inspected object and of opposite areas of the edge of the inspected object that are proximate to the apex; and a single optical element that is adapted to direct light towards the image sensor, from the apex of the edge of the inspected object and from the opposite areas of the edge of the inspected object that are proximate to the apex.

An optical inspection system that includes: an image sensor adapted to concurrently acquire images of an apex of the edge of the inspected object and of opposite areas of the edge of the inspected object that are proximate to the apex; and an array of fibers adapted to direct light towards the image sensor from the apex of an edge of an inspected object and from the opposite areas of the edge of the inspected object that are proximate to the apex.

According to various embodiments of the invention each of the mentioned above systems can be characterized by one of more of the following characteristics or elements listed below (unless there is a contradiction between a mentioned above embodiments of the system and an characteristic or element mentioned below): (i) the optical element is a multi-facet reflector; (ii) the optical element directs light from substantially opposite areas of the edge of the inspected object towards the image sensor; (iii) the optical element directs light from a top bevel area and from a bottom bevel area of the edge of the inspected object towards the image sensor; (iv) the optical element directs light from an apex and from at least one bevel area out of a top bevel area and a bottom bevel area of the edge of the inspected object towards the image sensor; (v) the optical element directs light from a top bevel area and a bottom area of the edge of the inspected object; (vi) the optical element directs light from a bottom bevel area and a top area of the edge of the inspected object towards the image sensor; (vii) the optical element directs light from a top bevel area, an apex area and from a top area of the edge of the inspected object towards the image sensor; (viii) the optical element directs light from a bottom bevel area, an apex area and a bottom area of the edge of the inspected object towards the image sensor; (ix) the optical element directs light from at least four areas out of a top area, a top bevel area, a bottom bevel area, an apex area and a bottom area of the edge of the inspected object towards the image sensor; (x) the optical element directs light from a top area, a top bevel area, a bottom bevel area, an apex area and a bottom area of the edge of the inspected object towards the image sensor; (xi) the optical element is adapted to reduce a length difference between different optical paths defined between the different areas and the image sensor; (xii) the system includes a path length adjustment optics that reduces a length difference between different optical paths defined between the different areas and the image sensor; (xiii) the system includes a path length adjustment optics; wherein the path length adjustment optics and the optical element substantially equalize a length of different optical paths defined between the different areas and the image sensor; (xiv) the system includes an inspected object stabilizer that maintains a substantially constant distance between an illuminated portion of the edge of the inspected object and the optical element during a movement of the inspected object in relation to the optical element; (xv) the system includes an optical element mover adapted to move the optical element in relation to an illuminated portion of the edge of the inspected object in response to an estimated location of the illuminated portion of the edge of the inspected object, during a scan of the edge of the inspected object in relation to the optical element; (xvi) the optical element includes multiple portions that differ from each other by at least one optical characteristic; and wherein at a given point of time the different portions of the optical element direct, towards the image sensor, light from different regions of the edge of the inspected element; wherein each region of the edge of the inspected element includes at least two areas of the edge of the inspected element that are oriented in relation to each other; (xvii) the optical element includes multiple portions that differ from each other by at least one optical characteristic; and wherein at a given point of time the different portions of the optical element direct, towards the image sensor, light from different regions of the edge of the inspected element; wherein each region of the edge of the inspected element has an central axis that is substantially perpendicular to a plane defined by an upper surface of the inspected object; (xviii) the image sensor is an area image sensor; (xix) the image sensor is a linear image sensor; (xx) the single optical element includes at least one penta-prism.

A method for inspecting an edge of an inspected object, the method includes: illuminating the edge of the inspected object; directing light from different areas of the edge of the inspected object towards an image sensor, by a single optical element, that at least partially surrounds an edge of an inspected object, towards the image sensor; and concurrently obtaining, by the image sensor, images of the different areas.

A method for inspecting an edge of an inspected object, the method includes: illuminating the edge of the inspected object; directing light from different areas of the edge of the inspected object towards an image sensor, by multiple optic fibers that are arranged such as to at least partially surround the edge of an inspected object; concurrently acquiring, by the image sensor, images of the different areas.

A method for inspecting an edge of an inspected object, the method includes: illuminating the edge of the inspected object; directing light, by a single optical element, from an apex of an edge of an inspected object and from opposite areas of the edge of the inspected object that are proximate to the apex towards an image sensor; and concurrently acquiring images, by the image sensor, of the apex of the edge of the inspected object and from the opposite areas of the edge of the inspected object that are proximate to the apex.

A method for inspecting an edge of an inspected object, the method includes: illuminating the edge of the inspected object; directing light, by an array of fibers, from an apex of an edge of an inspected object and from opposite areas of the edge of the inspected object that are proximate to the apex, towards an image sensor; and concurrently acquiring images, by the image sensor, of the apex of the edge of the inspected object and from the opposite areas of the edge of the inspected object that are proximate to the apex.

According to various embodiments of the invention each of the mentioned above methods can be characterized by one of more of the following characteristics or stages listed below (unless there is a contradiction between a mentioned above embodiment of the method and a characteristic or element mentioned below): (i) directing light by an optical element that is a multi-facet reflector; (ii) directing light from substantially opposite areas of the edge of the inspected object towards the image sensor; (iii) directing light from a top bevel area and from a bottom bevel area of the edge of the inspected object towards the image sensor; (iv) directing light from an apex and from at least one bevel area out of a top bevel area and a bottom bevel area of the edge of the inspected object towards the image sensor; (v) directing light from a top bevel area and a bottom area of the edge of the inspected object; (vi) directing light from a bottom bevel area and a top area of the edge of the inspected object towards the image sensor; (vii) directing light from a top bevel area, an apex area and from a top area of the edge of the inspected object towards the image sensor; (viii) directing light from a bottom bevel area, an apex area and a bottom area of the edge of the inspected object towards the image sensor; (ix) directing light from at least four areas out of a top area, a top bevel area, a bottom bevel area, an apex area and a bottom area of the edge of the inspected object towards the image sensor; (x) directing light from a top area, a top bevel area, a bottom bevel area, an apex area and a bottom area of the edge of the inspected object towards the image sensor; (xi) reducing, by the optical element, a length difference between different optical paths defined between the different areas and the image sensor; (xii) reducing, by a path length adjustment optics, a length difference between different optical paths defined between the different areas and the image sensor; (xiii) substantially equalizing, by a path length adjustment optics and the optical element, a length of different optical paths defined between the different areas and the image sensor; (xix) maintaining, by an inspected object stabilizer, a substantially constant distance between an illuminated portion of the edge of the inspected object and the optical element during a movement of the inspected object in relation to the optical element; (xx) moving, by an optical element mover, the optical element in relation to an illuminated portion of the edge of the inspected object in response to an estimated location of the illuminated portion of the edge of the inspected object, during a scan of the edge of the inspected object in relation to the optical element; (xxi) directing, at a given point of time and by the different portions of the optical element, towards the image sensor, light from different regions of the edge of the inspected element; wherein each region of the edge of the inspected element comprises at least two areas of the edge of the inspected element that are oriented in relation to each other; wherein the optical element comprises multiple portions that differ from each other by at least one optical characteristic; (xxii) directing, at a given point of time and by the different portions of the optical element, towards the image sensor, light from different regions of the edge of the inspected element; wherein each region of the edge of the inspected element has an central axis that is substantially perpendicular to a plane defined by an upper surface of the inspected object; wherein the optical element comprises multiple portions that differ from each other by at least one optical characteristic; (xxiii) directing light towards an image sensor that is an area image sensor; (xxiv) directing light towards an image sensor that is a linear image sensor; and (xxv) directing light by a single optical element that includes at least one penta-prism.

BRIEF DESCRIPTION OF THE DRAWINGS

The foregoing and other objects, features, and advantages of the present invention will become more apparent from the following detailed description when taken in conjunction with the accompanying drawings. In the drawings, similar reference characters denote similar elements throughout the different views, in which:

FIG. 16 is a flow chart according to an embodiment of the invention.

DETAILED DESCRIPTION OF THE DRAWINGS

An optical inspection system and a method are provided. The inspection system and method can detect defects that are close to the edge of an inspected object (such as, but not limited to, a wafer). The system is able to illuminate multiple facets of the object concurrently and detect light reflected and/or scattered from these illuminated facets. The detection can be implemented by using a single image sensor, such as but not limited to a video camera.

The system defines multiple optical paths that deflect light rays reflected from each facet of interest such that all light rays are focused on the image sensor surface.

The system and method can be utilized for various purposes (applications) such as but not limited to detection of defects of various sizes, down to micron-level defects in the top, top near-edge, apex, bottom near-edge and bottom surfaces at the periphery of thin substrates, such as wafers used in the production of semiconductor or MEMS devices, or solar cells.

A method is provided. The method includes: illuminating a multi-facet object using a multi-facet deflector; collecting light reflected and, additionally or alternatively, scattered from multiple facets of the object while using the multi-facet deflector; and detecting defects based upon the collected light. Conveniently two opposing facets of the multi-facets are illuminated concurrently during the illuminating. Conveniently, the illuminating includes illuminating the multi-facet object by a multi-facet deflector that includes light guides.

For simplicity of explanation, some of the following figures refer to a wafer. It is noted that other inspected objects (such as but not limited to a thin substrate) can be inspected by either one of the below mentioned systems and by either one of the below mentioned methods.

Figure 1:
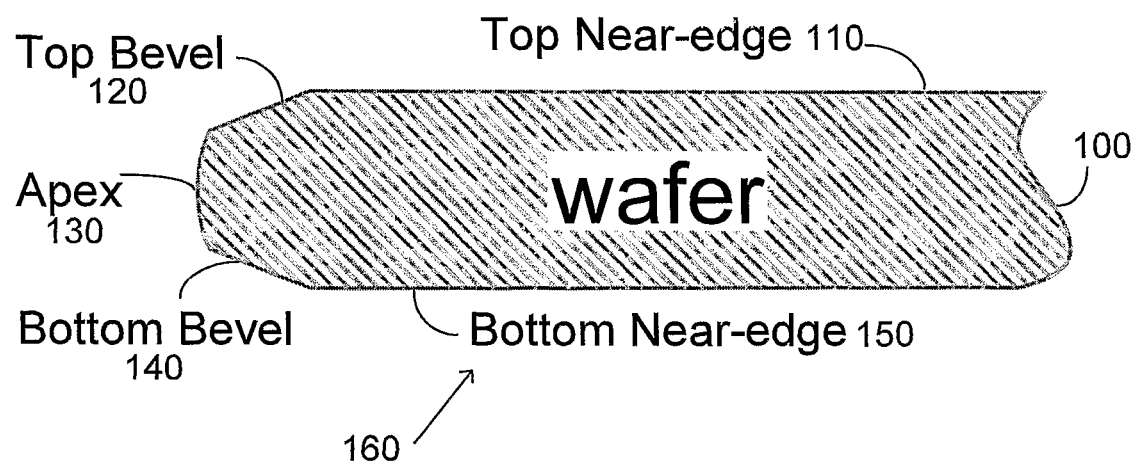
FIG. 1 illustrates an edge of a wafer.

FIG. 1 depicts a cross section of an edge of an inspected object such as wafer 100.

Edge 160 of wafer 100 includes five surfaces (facets) of interest that the method and system can inspect simultaneously—top facet 110, top bevel facet 120, apex 130, bottom bevel facet 140 and bottom facet 150. It is noted that top facet 110 and bottom facet 150 can extend out of edge 160. For simplicity of explanation they are viewed as including only portions of these facets that are proximate to apex 130.

It is noted that the below mentioned methods and systems can be applied mutatis mutandis to inspect objects having fewer surfaces of interest, such as having a rectangular cross section, or more.

It is noted that in some of the following figures these numbers (110, 120, 130, 140 and 150) are not shown—for convenience of explanation only.

Figure 2:
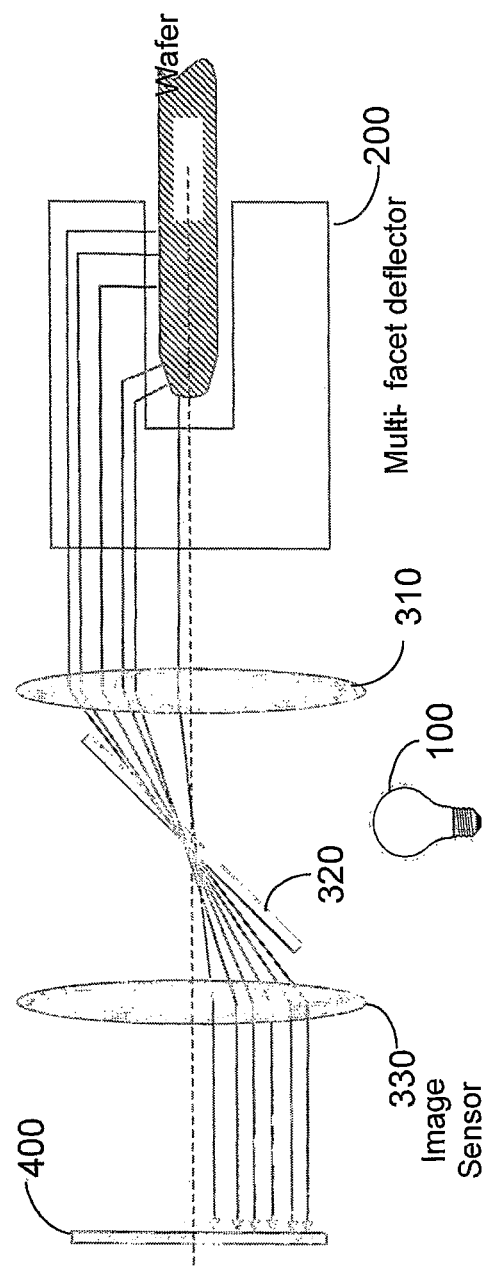
FIG. 2 illustrates a wafer and a system according to an embodiment of the invention.

FIG. 2 illustrates system 500 and wafer 100 according to an embodiment of the invention.

System 500 includes image sensor 400, light source 340, beam splitter 320, a pair of lenses 310 and 330 and a single optical element such as multi-facet deflector 200 that at least partially surrounds edge 160 of wafer 100.

System 500 can include one or more lenses, apertures, glare stops, optical length equalizers and alike.

It is noted that refractors can be used in addition to or instead of deflectors.

System 500 transfers images of different facets of edge 160 and projects it onto image sensor 400.

System 500 illustrates an on-axis illumination path that includes light source 340 and beam splitter 320. It can, additionally or alternatively, include other types of illumination paths such as tilted illumination. The light from an illumination path may be shone directly onto the object, or can pass through fiber optics or lenses. Light sources of system 500 can include incandescent lamps, LEDs, arc lamps, flash tubes, laser, and the like. A light source of system 500 can be continuous or intermittent, or any combination thereof. System 500 can also include at least one of the following components: image processor, stage, and the like. If, for example the inspected object is circular the stage can rotate the object about a central axis.

Multi-facet deflector 200 concurrently collects light reflected or scattered from multiple facets of wafer 100 and directs the collected light towards (even via additional optics such as lenses 310 and 330) image sensor 400. Multi-facet deflector 200 converts the set of images acquired from the various facets into a planar image.

Figure 3:
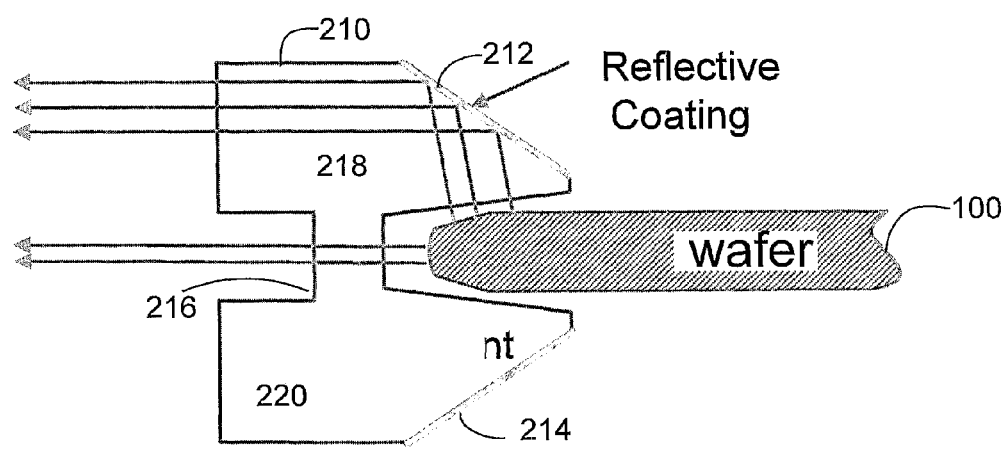
FIG. 3 illustrates an edge of a wafer and a optical element according to an embodiment of the invention.

In the example of FIG. 3 multi-facet deflector 210 includes three portions—upper portion 218 that collects light from top facet 110 and top bevel facet 120 of edge 160, middle portion 216 that collects light from apex 130 and lower portion 220 that collects light from bottom facet 150 and bottom bevel facet 140 of edge 160.

Multi-facet deflector 210 is followed by path length adjustment optics (not shown) that reduces the differences between the optical paths of light that passes through middle portion 216 and light that passes through upper portion 218 and lower portion 220. The difference in reduction can amount in equalizing the length of the different optical paths.

Path length adjustment optics is illustrated in PCT patent application serial number WO07129322A2 titled "SYSTEM AND METHOD FOR IMAGING OBJECTS" which is incorporated herein by reference.

Path length adjustment optics can pass light through retarding lenses or other optical components that have higher refractive index than gas.

For example, it can include retarding lens between upper and lower portions 218 and 220 and image sensor 400 that will virtually shorten the optical length of optical paths associated with these portions.

The path length adjustment optics can include path folding mirrors. The first folding mirror is positioned and angled with respect to the object's apex as to reflect an image of the apex to second folding mirror. The second mirror, in turn, is positioned and angled so as to reflect an image of the apex from first mirror to imaging sensor 400. Changing the distance between the first and second folding mirrors can determine the lengthening of the optical path of the top collection path.

Additionally or alternatively, multi-facet deflector 210 can reduce the difference as upper portion 218 and lower portion 218 and much wider (along an imaginary horizontal axis) than middle portion 216.

Multi-facet deflector 210 is made of optical grade, transparent material that is shaped such that light rays entering from facets 110, 120, 130, 140 and 150 are reflected toward image sensor 110, parallel to an imaginary optical axis that extends towards the image sensor. It is noted that although FIG. 3 illustrates a horizontal line this is not necessarily so. (It is noted that the entire system may be oriented in any direction, as long as the relative positions of the inspected object and described system are maintained).

In this embodiment this reflection is achieved by forming facet "a" 212 of upper portion 218 at an appropriate angle and coating it with reflective material or attaching a mirror to it. A similar embodiment can use internal reflection at facets "a" utilizing a prism principle. Facet "b" of lower and upper portions 218 and 220 can be undercut or drilled through to equalize the optical path lengths of the various light beams.

Figure 4:
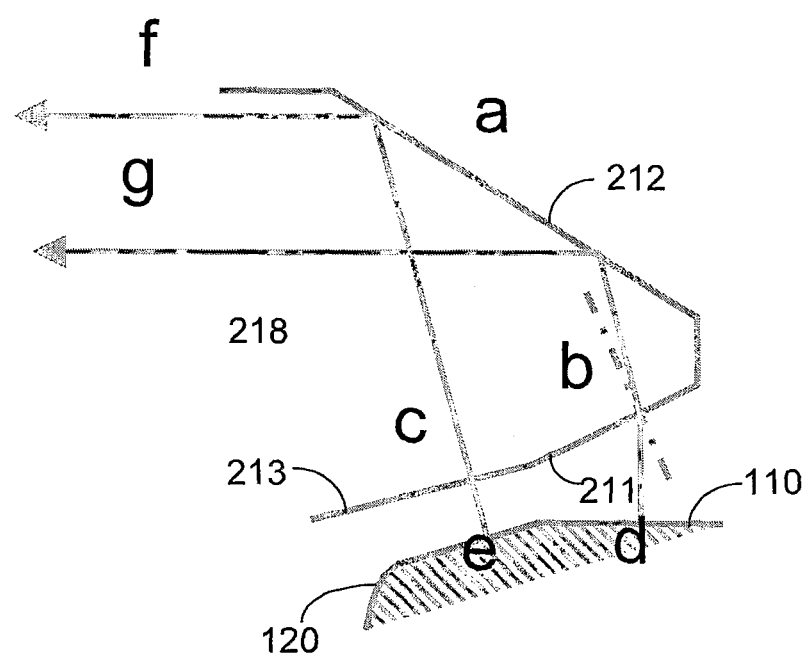
FIG. 4 illustrates a portion of an edge of a wafer and a portion of an optical element according to an embodiment of the invention.
Figure 5:
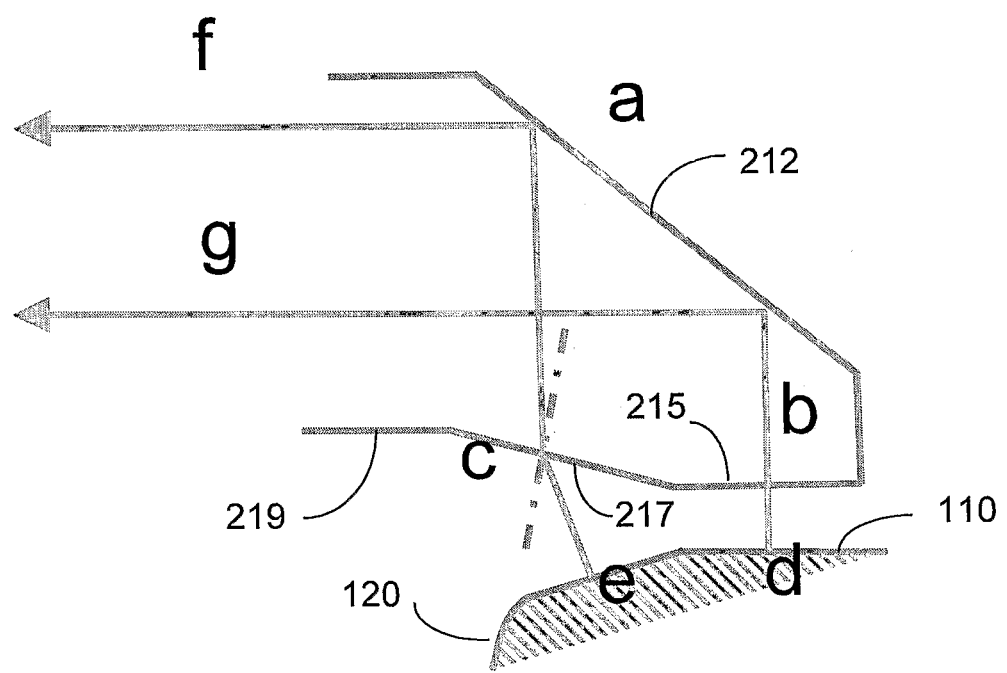
FIG. 5 illustrates a portion of an edge of a wafer and a portion of an optical element according to an embodiment of the invention.

FIGS. 4 and 5 illustrate cross sections of portions of multi-facet deflector according to various embodiments of the invention.

FIG. 4 illustrates facet "a" 212 that is formed at an angle smaller than 45° to the principle axis, such that a light beam "f" coming at a normal angle to top bevel facet ("e") of the object passes un-refracted through deflector facet "c" 213, hits the reflecting deflector facet "a" 212 and is reflected towards image sensor 400 in a parallel path to the principle axis. Deflector facet "b" 211 is angled such that a light beam "g" coming at a normal angle to top facet ("d") of the inspected object refracts as it crosses deflector facet "b" 211 and proceeds parallel to beam "f".

FIG. 5 illustrates a deflector facet "a" 212 that forms a 45° angle with the principle axis such that it reflects light beams at a straight angle. Light beam "f" refracts in crossing deflector facet "c" 217, while beam "g" emitted from top facet "d" 110 passes straight through deflector facet "b" 215 and proceeds parallel to beam "f".

Similar geometries can be applied to other shapes of inspected objects.

Figure 6:
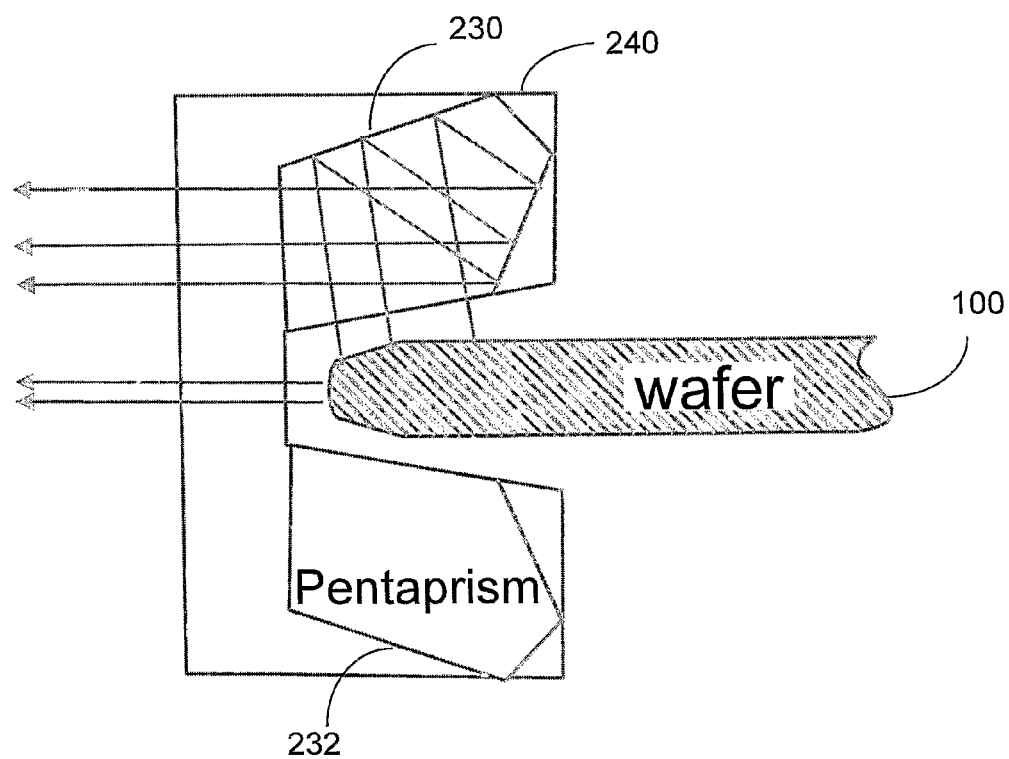
FIG. 6 illustrates an edge of a wafer, a top optical element and a bottom optical element according to an embodiment of the invention.

In the example of FIG. 6 an optical element includes a pair of multi-faceted prism such as a penta-prism. These are also referred to as a top optical element and a bottom optical element.

One penta-prism is located above the inspected object while the second penta-prism is located below the inspected object. Each penta-prism transfers an erect image and can better equalize optical path lengths of light that is reflected at different angles and/or from different locations of the objects. These penta-prisms can either be installed in a holding frame, or formed by machining a block made of transparent material. As illustrated in FIG. 5, the facets facing the inspected object can be further shaped to refract light beams at normal angles to the object's facets.

Figure 7:
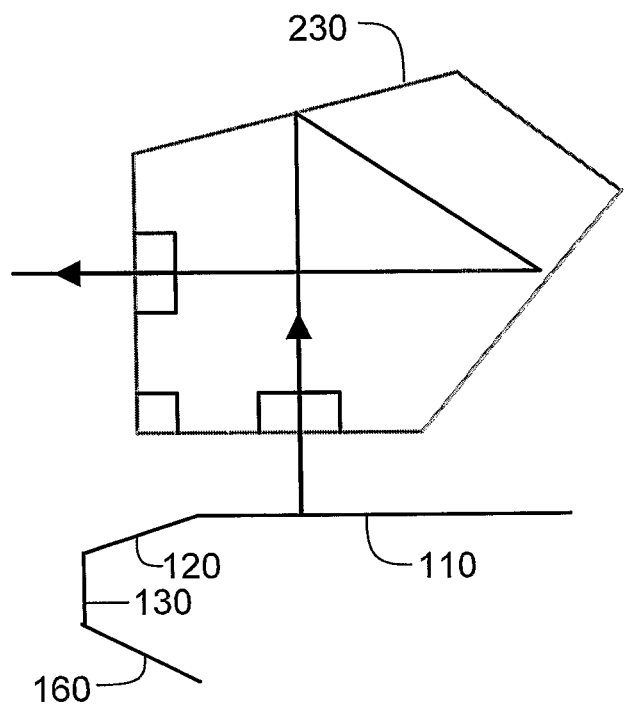
FIG. 7 illustrates an edge of a wafer and a top optical element according to an embodiment of the invention.

FIG. 7 illustrates multiple light rays that pass through the upper (top) penta-prism 230.

Figure 8:
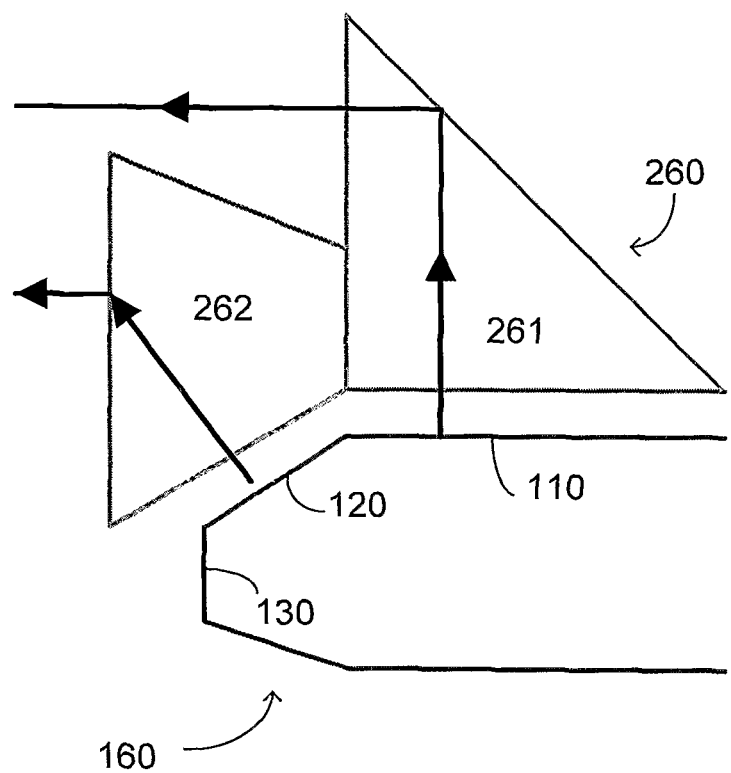
FIG. 8 illustrates a portion of an edge of a wafer and a portion of an optical element according to an embodiment of the invention.

FIG. 8 illustrates edge 160 (and some of its facets—110, 120 and 130) as well as a upper portion of a multi-facet deflector 260 that has multiple portions that differ from each other by their shape so that one portion 261 reflects light from top facet 110 towards an image sensor while the second portion 262 is shaped to reflect light from top bevel facet 120.

A deflecting facet of first portion 261 is oriented in an angle of 45° in relation to the horizon and deflects a vertical light from top facet 110 towards the horizon (towards image sensor).

A lower facet of second portion 262 is parallel to top bevel facet 120 while another facet is vertical. Light that is reflected at 90° from top bevel facet 120 is deflected by the vertical facet of second portion 262 by 135° and exits second portion 262 at a horizontal direction.

Figure 9:
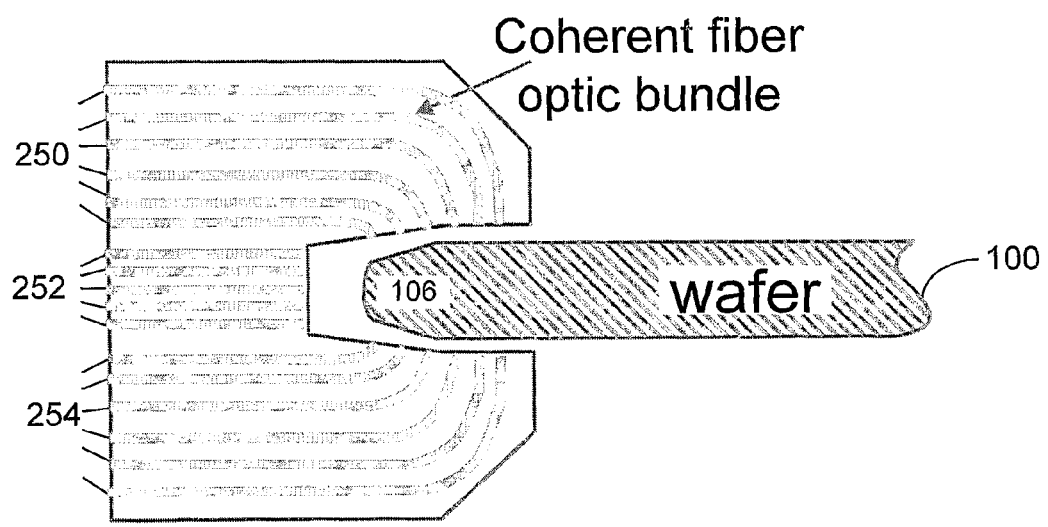
FIG. 9 illustrates multiple optic fibers and an edge of a wafer according to an embodiment of the invention.

FIG. 9 illustrates multiple fibers 250, 252 and 254 that are arranged such as to at least partially surrounds edge 106.

A first group of fibers 250 collects light from top facet 110 and from top bevel facet 120. A second group of fibers 252 collects light from apex 130. A third group of fibers 254 collects light from bottom facet 150 and from bottom bevel facet 140.

These fibers can be held by (integrated within) a multi-facet deflector but this is not necessarily so. The diameter and density of the fibers should match the required optical resolution.

Figure 10:
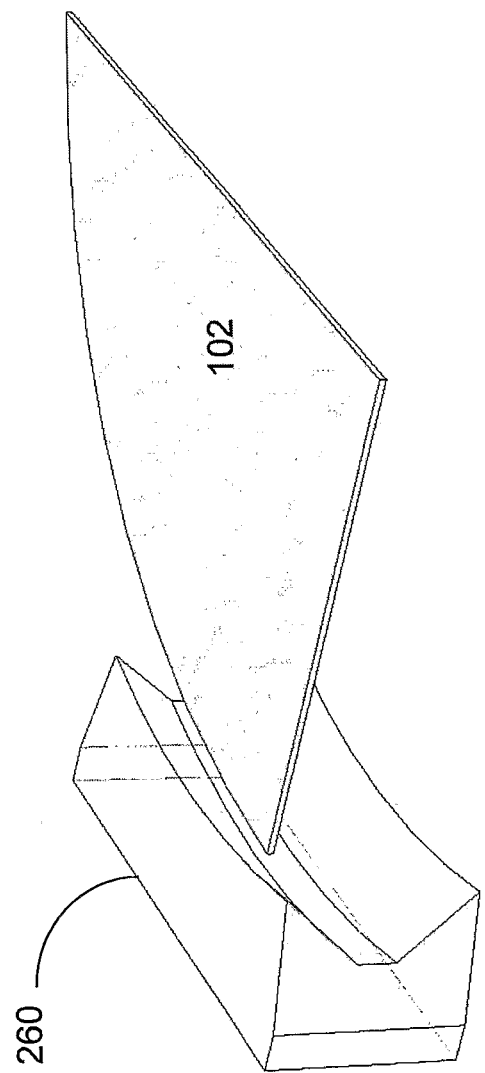
FIG. 10 illustrates a portion of a wafer and an optical element according to an embodiment of the invention.
Figure 11:
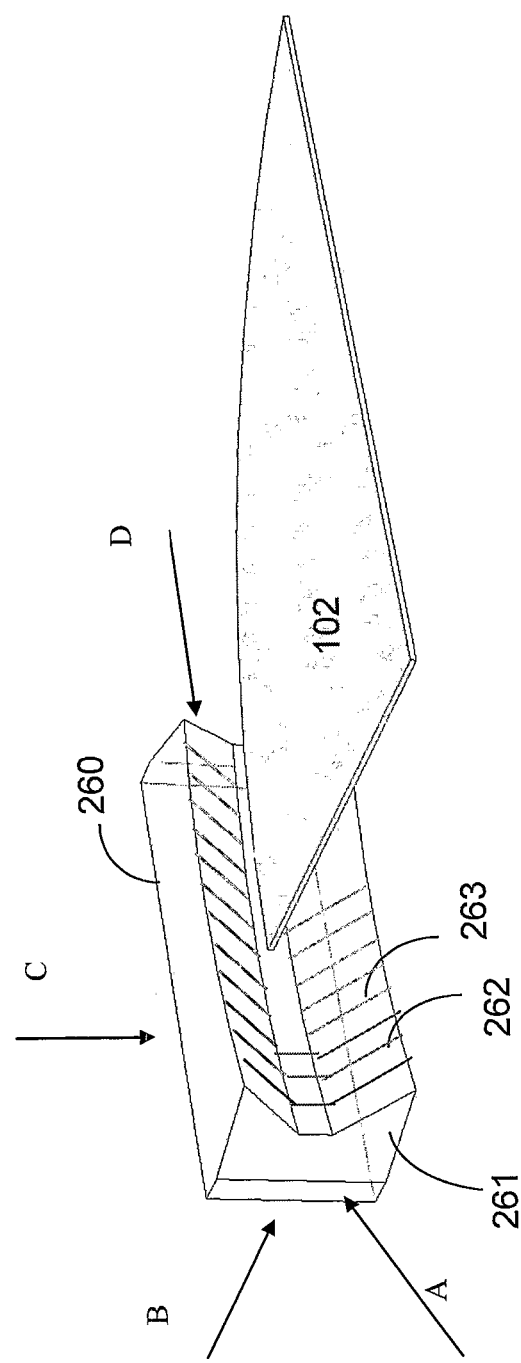
FIG. 11 illustrates a portion of a wafer and an optical element according to an embodiment of the invention.
Figure 12:
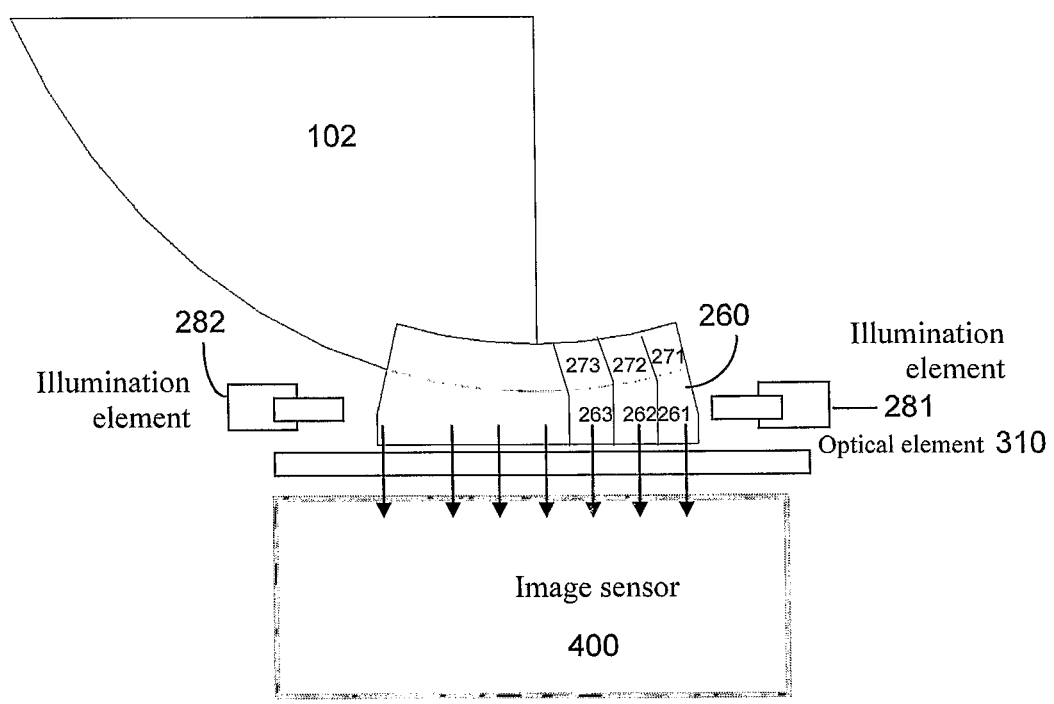
FIG. 12 illustrates a portion of a wafer, illumination elements, an optical element and an image sensor, according to an embodiment of the invention.

FIGS. 10 and 11 illustrate portion 102 of wafer (that rotates about its center) and optical element 260 according to an embodiment of the invention. Wafer 102 rotates about its center, as illustrated by the dashed curved arrow. FIG. 12 also illustrates illumination elements 281 and 282, optics elements 310 and image sensor 400.

Optical element 260 includes multiple sub elements (such as sub elements 261, 262 and 263) that differ from each other by at least one optical characteristic.

The difference can be introduced by a difference of at least one of the following characteristics of the sub element and especially of a surface of the each sub element: quality of surface, coating of surface, optical characteristic of a surface, geometrical shape of surface, material of surface, treatment of material of surface, optical characteristics of material, polarizing effect, depolarizing effect, and the like.

The above mentioned difference can introduce a difference in an illumination or light collection from each sub element of the wafer that is either illuminated by the sub element and, additionally or alternatively, from which light is collected by that sub element.

For example, when the edge of the wafer is illuminated from at least one of possible directions A, B, C and D the illumination or collection introduced by each sub element can differ by its angular coverage, magnification, polarization, intensity, color filter, spectral range, and the like.

During inspection wafer 102 is rotated around it center and explores it edge to each sub element out of 261, 262 and 263.

Image sensor 400 will grab images of wafer edge 160 through each of sub elements 261, 262 and 263 and can process each of the optically acquired information in various manners.

Accordingly, system 500 acquires, per each region of the wafer edge the system will acquire several images—according to the number of sub elements of optical element 260.

Sub regions 261, 262 and 263 collect light from regions 271, 272 and 273 of wafer 100. Each region can include a combination of at least two areas out of a top area, a top bevel area, an apex area, a bottom bevel area and a bottom area.

System 600 can process image information associated with each different sub element (261, 262 and 263) individually according to the pre-defined set of operators and rules and/or in any combination with data acquired from neighbor area of wafer edge according to the same or other pre-defined set of operators and rules.

System 600 can combine the results of the process and analysis of a set of several images representing appropriated area on wafer edge and will decide about flaws found and classify it according to the pre-defined set of operators and rules.

Figure 13:
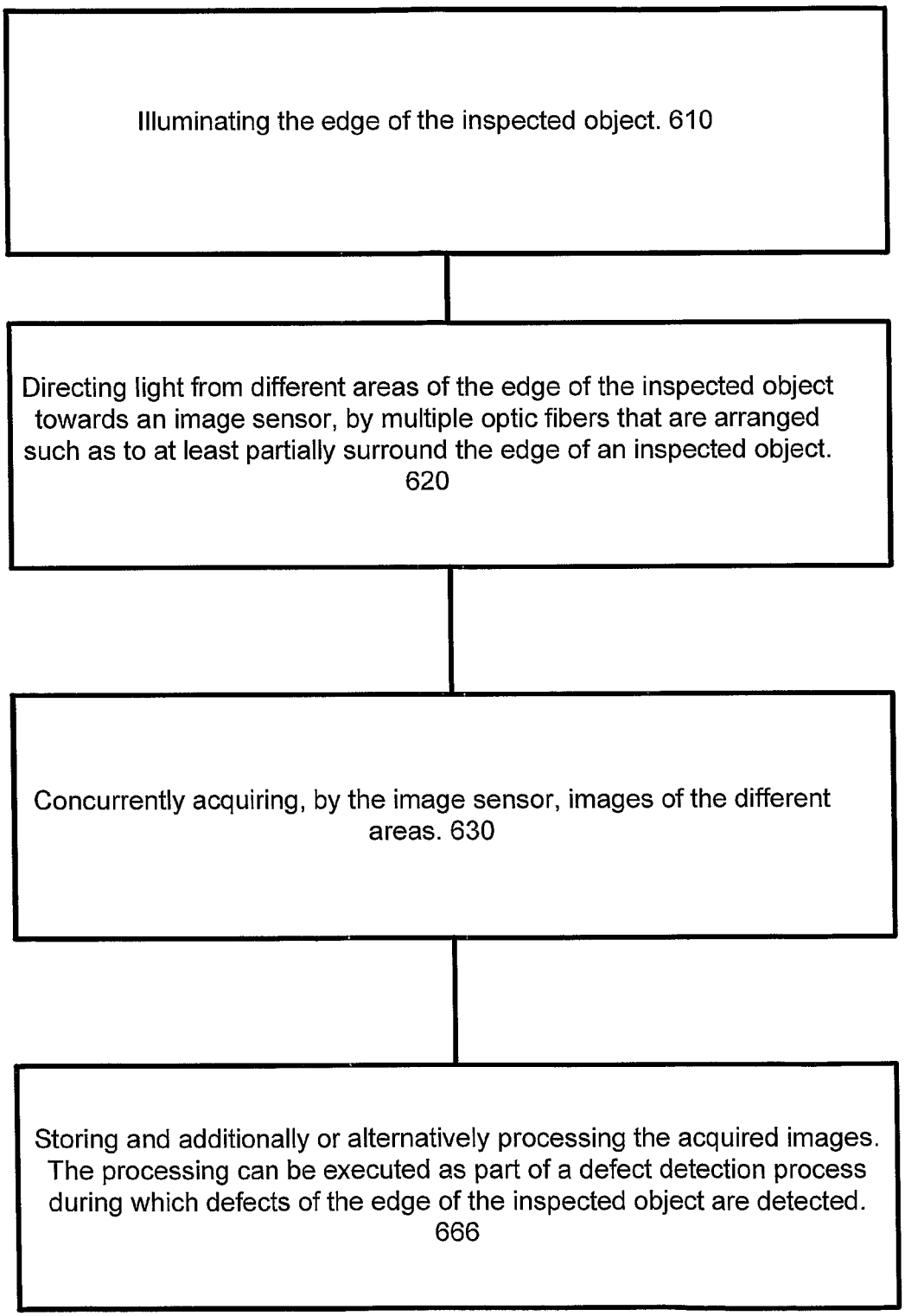
FIG. 13 is a flow chart according to an embodiment of the invention.

FIG. 13 illustrates method 600 for inspecting an edge of an inspected object, according to an embodiment of the invention.

Method 600 starts by stage 610 of illuminating the edge of the inspected object. The illumination can include on-axis illumination, off-axis illumination, pulsed illumination, continuous illumination, and the like.

Stage 610 is followed by stage 620 of directing light from different areas of the edge of the inspected object towards an image sensor, by multiple optic fibers that are arranged such as to at least partially surround the edge of an inspected object.

Each area can be a facet or a portion of a facet. A single facet can include multiple areas out of the different areas.

Stage 620 is followed by stage 630 of concurrently acquiring, by the image sensor, images of the different areas. Conveniently, these images do not overlap.

Stage 630 can be followed by stage 666 of storing and additionally or alternatively processing the acquired images. The processing can be executed as part of a defect detection process during which defects of the edge of the inspected object are detected. Thus stage 666 can include well known defect processing methods such as comparing to a reference, comparing one portion of the edge to another, comparing to expected results, and the like.

Method 600 can be executed by utilizing various systems and optical components, including but not limited to systems and optics illustrated in FIGS. 2, 3, 4, 5, 6, 7, 8, 10, 11 and 12.

Figure 14:
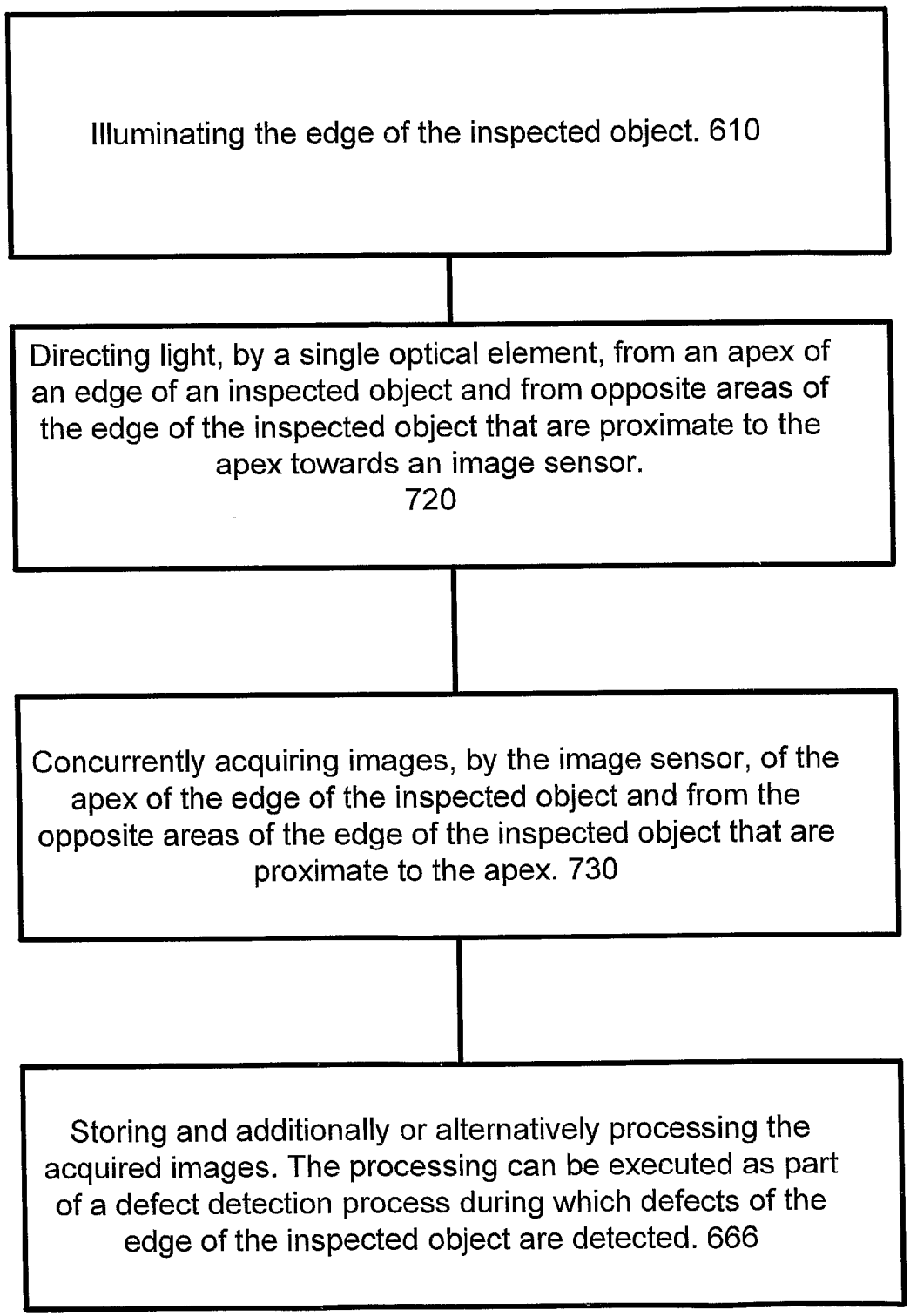
FIG. 14 is a flow chart according to an embodiment of the invention.

FIG. 14 illustrates method 700 for inspecting an edge of an inspected object, according to an embodiment of the invention.

Method 700 starts by stage 610 of illuminating the edge of the inspected object.

Stage 610 is followed by stage 720 of directing light, by a single optical element, from an apex of an edge of an inspected object and from opposite areas of the edge of the inspected object that are proximate to the apex towards an image sensor.

Stage 720 is followed by stage 730 of concurrently acquiring images, by the image sensor, of the apex of the edge of the inspected object and from the opposite areas of the edge of the inspected object that are proximate to the apex.

Stage 730 can be followed by stage 666 of storing and additionally or alternatively processing the acquired images. The processing can be executed as part of a defect detection process during which defects of the edge of the inspected object are detected. Thus stage 666 can include well known defect processing methods such as comparing to a reference, comparing one portion of the edge to another, comparing to expected results, and the like.

Method 700 can be executed by utilizing various systems and optical components, including but not limited to systems and optics illustrated in FIGS. 2, 3, 4, 5, 8, 10, 11 and 12.

Figure 15:
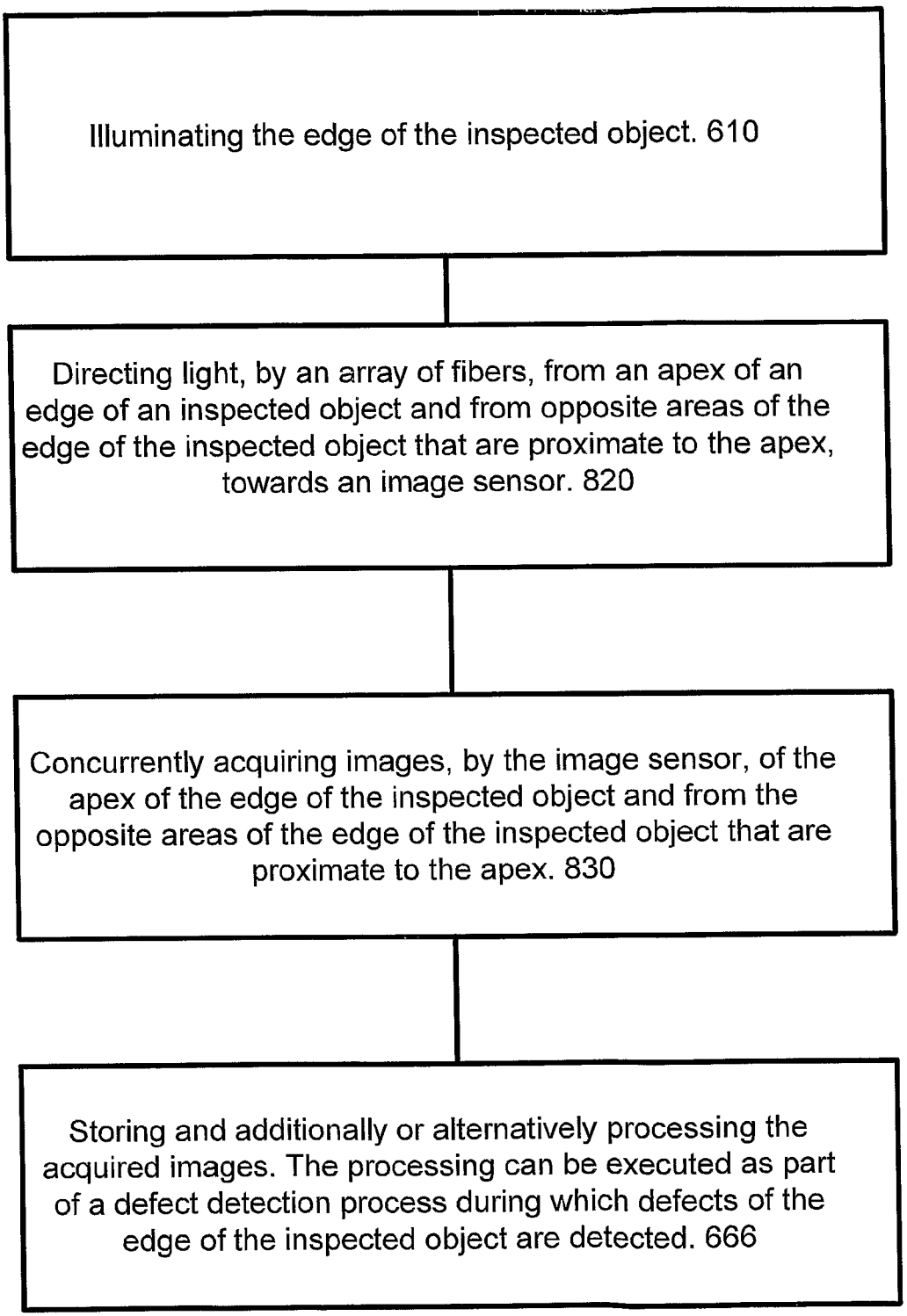
FIG. 15 is a flow chart according to an embodiment of the invention.

FIG. 15 illustrates method 800 for inspecting an edge of an inspected object, according to an embodiment of the invention.

Method 800 starts by stage 610 of illuminating the edge of the inspected object.

Stage 610 is followed by stage 820 of directing light, by an array of fibers, from an apex of an edge of an inspected object and from opposite areas of the edge of the inspected object that are proximate to the apex, towards an image sensor.

Stage 820 is followed by stage 830 of concurrently acquiring images, by the image sensor, of the apex of the edge of the inspected object and from the opposite areas of the edge of the inspected object that are proximate to the apex.

Stage 830 can be followed by stage 666 of storing and additionally or alternatively processing the acquired images. The processing can be executed as part of a defect detection process during which defects of the edge of the inspected object are detected. Thus stage 666 can include well known defect processing methods such as comparing to a reference, comparing one portion of the edge to another, comparing to expected results, and the like.

Method 600 can be executed by utilizing various systems and optical components, including but not limited to systems and optics illustrated in FIG. 9.

FIG. 16 illustrates method 900 for inspecting an edge of an inspected object, according to an embodiment of the invention.

Method 900 starts by stage 610 of illuminating the edge of the inspected object.

Stage 610 is followed by stage 920 of directing light, by optics positioned between the edge of the inspected object and an image sensor, towards an image sensor and reducing a length difference between different optical paths defined between different imaged areas of the edge of the inspected object and the image sensor. The optics include: a top optical element that directs light from at least one area out of a top area, a top bevel area and an apex of the edge of the inspected object towards the image sensor; and a bottom optical element that directs light from at least one area out of a bottom area, a bottom bevel area and an apex of the edge of the inspected object towards the image sensor.

Stage 920 is followed by stage 930 of concurrently acquiring images, by the image sensor, of the different imaged areas.

Stage 930 can be followed by stage 666 of storing and additionally or alternatively processing the acquired images. The processing can be executed as part of a defect detection process during which defects of the edge of the inspected object are detected. Thus stage 666 can include well known defect processing methods such as comparing to a reference, comparing one portion of the edge to another, comparing to expected results, and the like.

Method 900 can be executed by utilizing various systems and optical components, including but not limited to systems and optics illustrated in FIGS. 2, 3, 4, 5, 6, 7, 8, 10, 11 and 12.

It is noted that any combination of stages of any method out of methods 600, 700, 800 and 900 can be provided, as long as the combination does not include stages that contradict each other.

The present invention can be practiced by employing conventional tools, methodology, and components. Accordingly, the details of such tools, component, and methodology are not set forth herein in detail. In the previous descriptions, numerous specific details are set forth, in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. An optical inspection system, comprising:
   an image sensor;
   an optical element, that is a multi-facet reflector that at least partially surrounds an edge of an inspected object; wherein the optical element is adapted to (a) pass light that is normal to an apex area of the edge towards the apex area, (b) reflect light towards different areas of the edge that differ from the apex area, wherein the different areas comprise a top area, a top bevel area, a bottom area and a bottom bevel area; (c) and reflect light scattered or reflected from the apex area and from the different areas towards the image sensor so that the image sensor concurrently obtains images of the different areas and of the apex area; wherein the different areas are oriented to each other;
   a pair of lenses; and
   a beam splitter that is located between the pair of lenses, wherein the pair of lenses are parallel to each other and are positioned between the image sensor and the optical element;
   wherein the beam splitter is configured to reflect light from a light source towards the optical element; and
   wherein the pair of lenses are configured to direct light reflected from the top area and the top bevel area towards a part of the image sensor that is located below an optical axis of the image sensor.

2. The system according to claim 1 wherein the optical element comprises (a) an upper portion that is arranged to collect light from the top area and from the top bevel area, (b) a middle portion that is arranged to collect light from the apex area, and (c) a lower portion that is arranged to collect light from the bottom area and from the bottom bevel area.

3. The system according to claim 2 wherein the upper portion and the lower portion are normal to the apex area and are parallel to an optical axis of the image sensor.

4. The system according to claim 2 wherein a distance between a right end of the middle portion and a left end of the middle portion is smaller than each one of (a) a distance between a right end and a left end of the top portion and (b) a distance between a right end and a left end of the bottom portion.

5. The system according to claim 2 wherein the bottom portion and the top portion are arranged in a symmetrical manner about the middle portion.

6. The system according to claim 1 wherein the optical element is arranged to reflect light from the apex area and from any of the different areas of the edge in parallel to an optical axis of the image sensor.

7. The system according to claim 1 wherein the optical element comprises a first facet, a second facet, a third facet and a fourth facet, wherein the first facet and the second facet have a positive slope and are oriented to each other, wherein the fourth facet has a negative slope and is positioned above the first facet and the second facet, wherein an upper end of the third facet contacts a lower end of the fourth facet and wherein a lower end of the third facet contacts an upper end of the second facet.

8. The system according to claim 1 wherein the optical element comprises a first facet, a second facet, a third facet and a fourth facet, wherein the first facet has a negative slope, the fourth facet has negative slope and is positioned above the first facet and the second facet, wherein an upper end of the third facet contacts a lower end of the fourth facet and wherein a lower end of the third facet contacts an upper end of the second facet.

9. The system according to claim 1 wherein the optical element is adapted to reduce a length difference between different optical paths defined between the different areas and the image sensor.

10. The system according to claim 1 comprising a path length adjustment optics that reduces a length difference between different optical paths defined between the different areas and the image sensor.

11. The system according to claim 1 comprising a path length adjustment optics; wherein the path length adjustment optics and the optical element substantially equalize a length of different optical paths defined between the different areas and the image sensor.

12. The system according to claim 1 comprising an inspected object stabilizer that maintains a substantially constant distance between an illuminated portion of the edge of the inspected object and the optical element during a movement of the inspected object in relation to the optical element.

13. The system according to claim 1 comprising an optical element mover adapted to move the optical element in relation to an illuminated portion of the edge of the inspected object in response to an estimated location of the illuminated portion of the edge of the inspected object, during a scan of the edge of the inspected object in relation to the optical element.

14. The system according to claim 1 wherein the optical element comprises multiple portions that differ from each other by at least one optical characteristic; and wherein at a given point of time the different portions of the optical element direct, towards the image sensor, light from different regions of the edge of the inspected element; wherein each region of the edge of the inspected element comprises at least two areas of the edge of the inspected element that are oriented in relation to each other.

15. The system according to claim 1 wherein the optical element comprises multiple portions that differ from each other by at least one optical characteristic; and wherein at a given point of time the different portions of the optical element direct, towards the image sensor, light from different regions of the edge of the inspected element; wherein each region of the edge of the inspected element has an central axis that is substantially perpendicular to a plane defined by an upper surface of the inspected object.

16. The system according to claim 1 wherein the image sensor is an area image sensor.

17. The system according to claim 1 wherein the image sensor is a linear image sensor.

18. The system according to claim 1 wherein the inspected object is a wafer.

19. The system according to claim 1 wherein the optical element comprises a pair of penta-prisms that are symmetrically arranged about a symmetry axis of the optical element.

20. The system according to claim 1 wherein the optical element comprises multiple portions that differ from each other by angular coverage.

21. The system according to claim 1 wherein the optical element comprises multiple portions that differ from each other by magnification.

22. The system according to claim 1 wherein the optical element comprises multiple portions that differ from each other by color filtering.

23. The system according to claim 1 wherein the optical element comprises multiple portions that differ from each other by spectral range.

24. An optical inspection system, comprising: an image sensor; an optical element, that is a multi-facet reflector that at least partially surrounds an edge of an inspected object wherein the optical element is adapted to (a) pass light that is normal to an apex area of the edge towards the apex area, (b) reflect light towards different areas of the edge that differ from the apex area, wherein the different areas comprise a top area, a top bevel area, a bottom area and a bottom bevel area; (c) and reflect light scattered or reflected from the apex area and from the different areas towards the image sensor so that the image sensor concurrently obtains images of the different areas and of the apex area; wherein the different areas are oriented to each other; wherein the optical element comprises (a) an upper portion that is arranged to collect light from the top area and from the top bevel area, (b) a middle portion that is arranged to collect light from the apex area, and (c) a lower portion that is arranged to collect light from the bottom area and from the bottom bevel area; wherein the middle portion is configured to pass light towards the image sensor while maintaining a direction of propagation of the light and wherein the top portion comprises a oriented reflecting facet that is configured to reflect light from the top area and the top bevel area towards the light sensor.

* * * * *